US00PP34800P2

(12) United States Plant Patent
van Dijk

(10) Patent No.: US PP34,800 P2
(45) Date of Patent: Dec. 6, 2022

(54) ***HYDRANGEA* PLANT NAMED 'HIOCE'**

(50) Latin Name: *Hydrangea macrophylla*
Varietal Denomination: HIOCE

(71) Applicant: Roy Robin van Dijk, De Lier (NL)

(72) Inventor: Roy Robin van Dijk, De Lier (NL)

(73) Assignee: HI BREEDING B.V., DeLier (NL)

( * ) Notice: Subject to any disclaimer, the term of this patent is extended or adjusted under 35 U.S.C. 154(b) by 31 days.

(21) Appl. No.: 17/688,824

(22) Filed: Mar. 7, 2022

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — C. Anne Whealy

(57) ABSTRACT

A new and distinct cultivar of *Hydrangea* plant named 'HIOCE', characterized by its upright and broadly spreading plant habit; moderately vigorous growth habit and moderate growth rate; freely branching habit; strong and sturdy stems; dark green-colored leaves; freely flowering habit; large and dense inflorescences with purplish red-colored sterile flowers; and good post-production longevity.

3 Drawing Sheets

Figure 1:
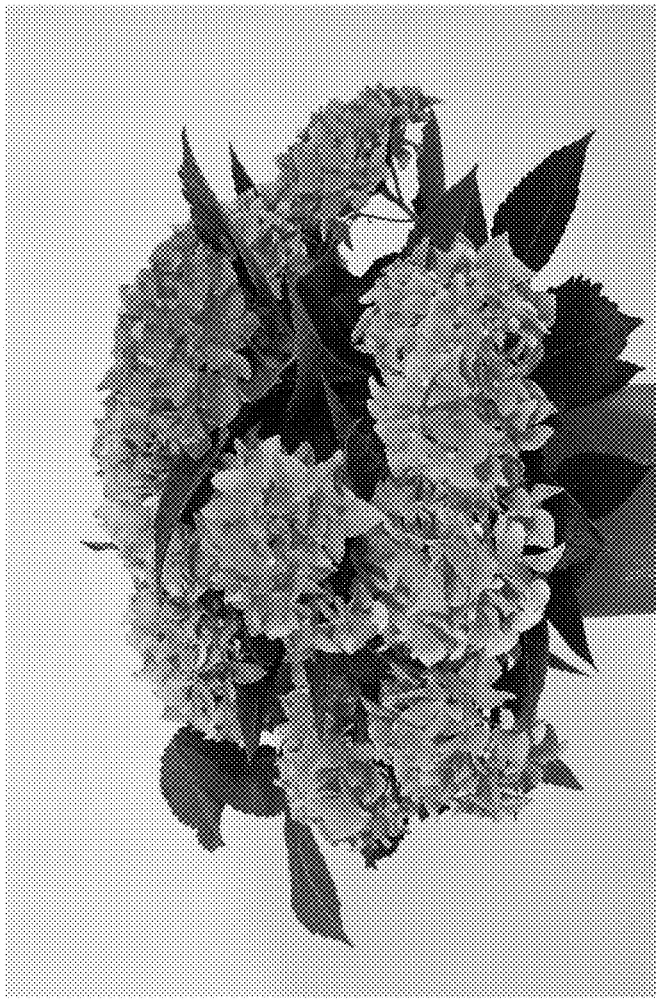

Botanical designation: *Hydrangea macrophylla.*
Cultivar denomination: 'HIOCE'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Hi Breeding B.V. of De Lier, The Netherlands on Nov. 15, 2021, application number 2021/2938. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIOCE'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination on Apr. 7, 2017 of a proprietary selection of *Hydrangea macrophylla* identified as code number 1563, not patented, as the female, or seed, parent with a proprietary selection of *Hydrangea macrophylla* identified as code number 1671, not patented, as the male, or pollen, parent. The new *Hydrangea* plant was discovered and selected as a single flowering plant from within the progeny of the stated cross-pollination in a controlled greenhouse environment in De Lier, The Netherlands on Apr. 12, 2019.

Asexual reproduction of the new *Hydrangea* plant by terminal vegetative cuttings since Jul. 12, 2019 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIOCE'. These characteristics in combination distinguish 'HIOCE' as a new and distinct *Hydrangea* plant:

1. Upright and broadly spreading plant habit.
2. Moderately vigorous growth habit and moderate growth rate.
3. Freely branching habit.
4. Strong and sturdy stems.
5. Dark green-colored leaves.
6. Freely flowering habit.
7. Large and dense inflorescences with purplish red-colored sterile flowers.
8. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* are not as vigorous as plants of the female parent selection.
2. Plants of the new *Hydrangea* are more resistant to Botrytis than plants of the female parent selection.

Plants of the new *Hydrangea* can be compared to plants of the male parent selection. Plants of the new *Hydrangea* differ primarily from plants of the male parent selection in the following characteristics:

1. Stems of plants of the new *Hydrangea* are sturdier than stems of plants of the male parent selection.
2. Sepals of sterile flowers of plants of the new *Hydrangea* have acute apices whereas sepals of sterile flowers of plants of the male parent selection have rounded apices.

Plants of the new *Hydrangea* can be compared to plants of *Hydrangea macrophylla* 'HBA 202911', not patented. In side-by-side comparisons, plants of the new *Hydrangea* differ primarily from plants of 'HBA 202911' in the following characteristics:

1. Stems of plants of the new *Hydrangea* are sturdier than stems of plants of 'HBA 202911'.
2. Sepals of sterile flowers of plants of the new *Hydrangea* have acute apices whereas sepals of sterile flowers of plants of 'HBA 202911' have rounded apices.

Plants of the new *Hydrangea* can also be compared to plants of *Hydrangea macrophylla* 'LAVBLAA', not patented. In side-by-side comparisons, plants of the new *Hydrangea* differ primarily from plants of 'LAVBLAA' in the following characteristics:

1. Stems of plants of the new *Hydrangea* are sturdier than stems of plants of 'LAVBLAA'.
2. Sepals of sterile flowers of plants of the new *Hydrangea* have acute apices whereas sepals of sterile flowers of plants of 'LAVBLAA' have rounded apices.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HIOCE' grown in a container.

Figure 2:
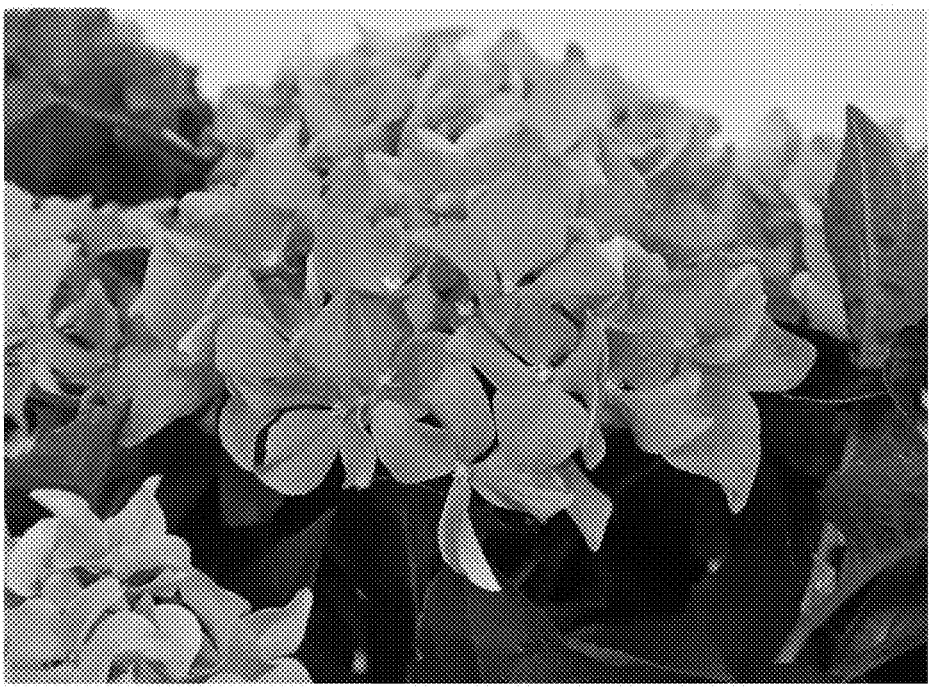

The photograph at the top of the second sheet (FIG. 2) is a close-up view of a typical inflorescence of 'HIOCE'.

Figure 3:
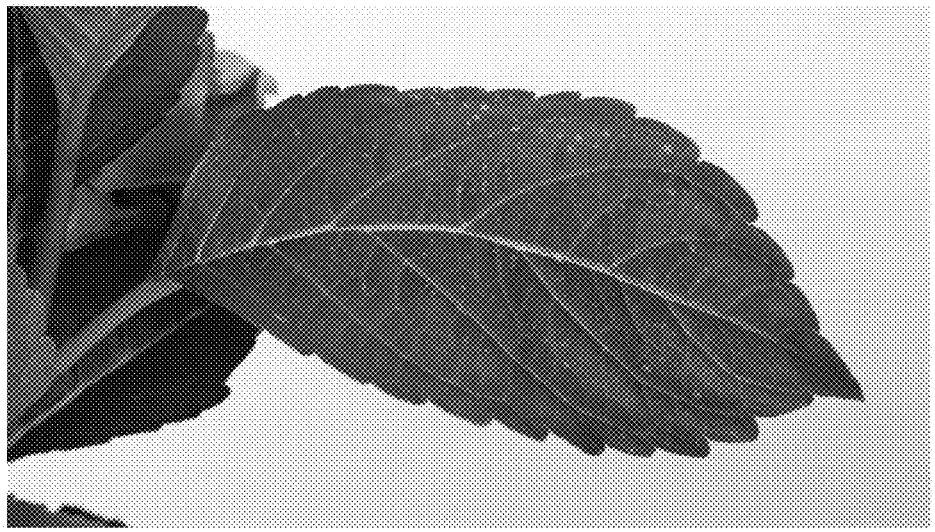

The photograph at the bottom of the second sheet (FIG. 3) is a close-up view of a typical leaf of 'HIOCE'.

Figure 4:
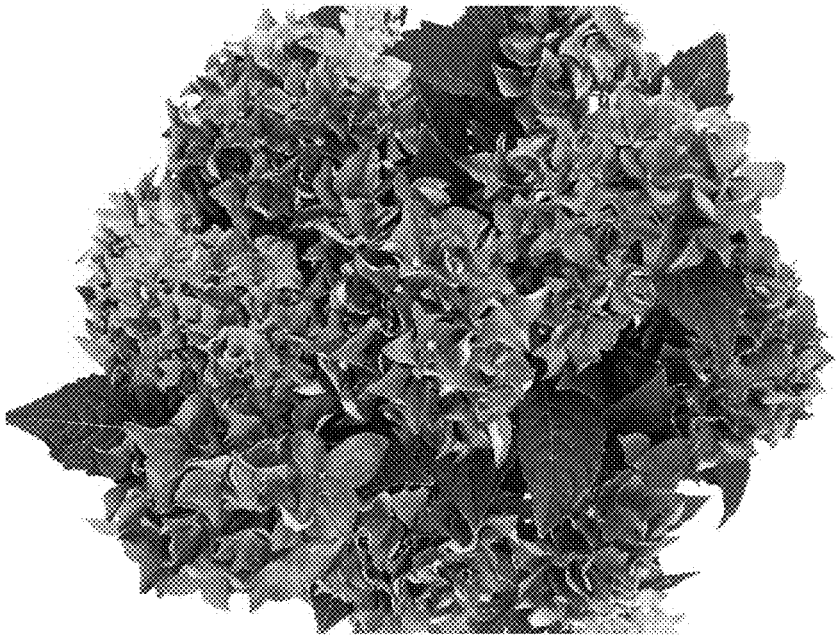

The photograph on the third sheet (FIG. 4) is a top perspective view of a typical flowering plant of 'HIOCE' that has been treated with aluminum sulfate, or "blued".

DETAILED BOTANICAL DESCRIPTION

Plants used in the aforementioned photographs and in the following description were grown during the late summer and early autumn in 14-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used.

Botanical description: *Hydrangea macrophylla* 'HIOCE'.

Parentage:

*Female, or seed, patent*.—Proprietary selection of *Hydrangea macrophylla* identified as code number 1563, not patented.

*Male, or pollen, patent*.—Proprietary selection of *Hydrangea macrophylla* identified as code number 1671, not patented.

Propagation:

*Type cutting*.—By vegetative terminal cuttings.

*Time to initiate roots, summer*.—About twelve days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About one month at temperatures about 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular to broadly obovate in overall shape; strong and sturdy stems; moderately vigorous and moderate growth rate; about six months from propagation are required to produce small finished flowering plants.

*Plant height*.—About 30.5 cm.

*Plant diameter or area of spread*.—About 54 cm.

Lateral branch description:

*Branching habit*.—Freely branching habit with about 17 lateral branches per plant; pinching enhances lateral branch development.

*Length*.—About 14.6 cm.

*Diameter*.—About 4.5 mm.

*Internode length*.—About 4.1 cm.

*Strength*.—Strong, sturdy.

*Aspect*.—About 45° from vertical.

*Texture, developing and developed*.—Smooth, glabrous; becoming woody with subsequent development.

*Color, developing*.—Close to 143B.

*Color, fully developed*.—Close to 144B; when woody, close to 199C and N199D.

*Lenticels*.—Density: Sparse. Length: About 0.1 mm. Diameter: About 0.04 mm. Color: Close to 200A and 200B.

Leaf description:

*Arrangement*.—Opposite, simple.

*Length*.—About 13.3 cm.

*Width*.—About 8 cm.

*Shape*.—Ovate.

*Apex*.—Apiculate.

*Base*.—Attenuate.

*Margin*.—Coarsely crenate-serrate.

*Texture, upper surface*.—Slightly rugose, glabrous.

*Texture, lower surface*.—Moderately rugose, glabrous.

*Venation pattern*.—Pinnate.

*Color*.—Developing leaves, upper surface: Close to 143A. Developing leaves, lower surface: Close to 144A. Fully developed leaves, upper surface: Close to NN137A tinged with close to N189A; venation, close to 146D. Fully developed leaves, lower surface: Close to 146A; venation, close to 146D.

*Petioles*.—Length: About 3.2 cm. Diameter: About 3.5 mm. Texture and luster, upper and lower surfaces: Smooth, glabrous; slightly glossy. Color, upper surface: Close to a 146D and towards the margins, close to 144A to 144B. Color, lower surface: Close to 144B.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly and fertile flowers mostly upright.

*Fragrance*.—None detected.

*Natural flowering season*.—In the garden, plants flower continuously from the late spring to late summer in The Netherlands; flower dormancy can be broken with a cold storage treatment.

*Flower longevity*.—Good postproduction longevity; sterile flowers maintain good substance for about six weeks on the plant, sterile flowers persistent; fertile flowers last for a few days on the plant, fertile flowers not persistent.

*Quantity of flowers*.—Freely flowering habit; about 65 sterile flowers per panicle and about 15 fertile flowers per panicle.

*Panicle height*.—About 8.9 cm.

*Panicle diameter*.—About 15.7 cm.

*Panicle peduncles*.—Length: About 4.6 cm. Diameter: About 3.5 mm. Strength: Strong. Aspect: Primary peduncles, mostly erect; lateral peduncles, about 45° from primary peduncle axis. Texture: Moderately pubescent. Color: Close to 145A.

*Sterile flower buds*.—Length: About 1.4 cm. Diameter: About 1.8 cm. Shape: Irregular and broadly cup-shaped. Color: Close to a blend of 63A and 63B.

*Fertile flower buds*.—Length: About 4 mm. Diameter: About 3.5 mm. Shape: Broadly obovate. Color: Close to 62C.

*Sterile flower diameter*.—About 3.7 cm to 6.6 cm.

*Sterile flower depth* (*height*).—About 1.8 cm.

*Fertile flower diameter*.—About 7 mm.

*Fertile flower depth* (*height*).—About 5 mm.

*Petals, sterile flowers*.—Quantity and arrangement: Four, or occasionally five, in a single whorl. Length: About 3 mm. Width: About 2 mm. Shape: Ovate, moderately concave. Apex: Acute. Base: Cuneate. Margin: Entire. Texture and luster, upper and lower surfaces: Smooth, glabrous; matte. Color: When opening and fully opened, upper surface: Close to 76B; color does not change with subsequent development. When opening and fully opened, lower surface: Close to 76B; color does not change with subsequent development.

*Petals, fertile flowers*.—Quantity and arrangement: Five in a single whorl. Length: About 3.5 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to 76B; color does not change with subsequent development. When opening and fully opened, lower surface: Close to 76B; color does not change with subsequent development.

*Sepals, sterile flowers*.—Quantity and arrangement: Typically four, or occasionally five, in a single whorl; strongly imbricate. Length: About 1.4 cm to 4.1 cm. Width: About 1 cm to 3.2 cm. Shape: Ovate to roughly rhomboidal, slightly concave. Apex: Bluntly acute. Base: Cuneate. Margin: Entire; slightly and coarsely undulate. Texture and luster, upper and lower surfaces: Smooth, glabrous; matte. Color: When opening, upper surface: Close to a blend of 58B and 61C. When opening, lower surface: Close to 70C. Fully opened, upper surface: Close to a blend of 63B and N66C; with subsequent development, color becoming closer to between 144B and 146D; when treated with aluminum sulfate or "blued", color becoming closer to N88A to N88B. Fully opened, lower surface: Close to 63C; with subsequent development, color becoming closer to 147D; when treated with aluminum sulfate or "blued", color becoming closer to N88B.

*Sepals, fertile flowers*.—Quantity and arrangement: Five in a single whorl. Length: About 1 mm. Width: About 1 mm. Shape: Broadly ovate to roughly deltoid. Apex: Acute. Base: Cuneate. Margin: Entire. Texture and luster, upper and lower surfaces: Smooth, glabrous; matte. Color: When opening and fully opened, upper surface: Close to 150D; color does not change with subsequent development. When opening and fully opened, lower surface: Close to 150D tinged with close to 62C; color does not change with subsequent development.

*Pedicels, sterile flowers*.—Length: About 2.3 cm. Diameter: About 1.25 mm. Strength: Moderately strong. Aspect: About 45° from main peduncle axis. Texture and luster: Moderately pubescent; matte. Color: Close to 70C.

*Pedicels, fertile flowers*.—Length: About 5.5 mm. Diameter: About 1 mm. Strength: Moderately strong. Aspect: About 15° from vertical. Texture and luster: Sparsely pubescent; matte. Color: Close to 70C.

*Reproductive organs, sterile flowers*.—Stamens: Quantity per flower: Eight. Filament length: About 3 mm. Filament color: Close to 76D. Anther shape: Broadly oblong. Anther length: About 0.5 mm. Anther color: Close to NN155A. Pollen amount: Scarce. Pollen color: Close to 156D. Pistils: Pistil quantity per flower: Two, or occasionally, one or three. Pistil length: About 1 mm. Stigma shape: Club-shaped. Stigma color: Close to NN155A. Style length: About 0.5 mm. Style color: Close to NN155A. Ovary color: Close to 157D.

*Reproductive organs, fertile flowers*.—Stamens: Quantity per flower: Ten. Filament length: About 3 mm.

Filament color: Close to 69D to lighter than 69D. Anther shape: Broadly oblong. Anther length: About 0.5 mm. Anther color: Close to NN155A. Pollen amount: Scarce. Pollen color: Close to 156D. Pistils: Pistil quantity per flower: Three, or occasionally two or four. Pistil length: About 1.5 mm. Stigma shape: Club-shaped. Stigma color: Close to NN155A. Style length: About 1 mm. Style color: Close to NN155A. Ovary color: Close to 157D.

*Seeds*.—To date, seed development has not been observed on plants of the new *Hydrangea*.

Pathogen & pest resistance: Plants of the new *Hydrangea* have been observed to be tolerant to Botrytis (*Botrytis cinerea*). To date, plants of the new *Hydrangea* have not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIOCE' as illustrated and described.

* * * * *